United States Patent
Duric et al.

(10) Patent No.: US 10,285,667 B2
(45) Date of Patent: May 14, 2019

(54) METHOD FOR GENERATING AN ENHANCED IMAGE OF A VOLUME OF TISSUE

(71) Applicant: Delphinus Medical Technologies, Inc., Plymouth, MI (US)

(72) Inventors: Nebojsa Duric, Plymouth, MI (US); Peter Littrup, Plymouth, MI (US); Cuiping Li, Plymouth, MI (US)

(73) Assignee: Delphinus Medical Technologies, Inc., Novi, MI (US)

( * ) Notice: Subject to any disclaimer, the term of this patent is extended or adjusted under 35 U.S.C. 154(b) by 855 days.

(21) Appl. No.: 14/819,091

(22) Filed: Aug. 5, 2015

(65) Prior Publication Data

US 2016/0038123 A1     Feb. 11, 2016

Related U.S. Application Data (60) Provisional application No. 62/033,265, filed on Aug. 5, 2014.

(51) Int. Cl.
    *A61B 8/00*        (2006.01)
    *A61B 8/08*        (2006.01)
    (Continued)

(52) U.S. Cl.
    CPC ............ *A61B 8/5207* (2013.01); *A61B 8/085* (2013.01); *A61B 8/0825* (2013.01); *A61B 8/14* (2013.01);
    (Continued)

(58) Field of Classification Search
None
See application file for complete search history.

(56) References Cited

U.S. PATENT DOCUMENTS 3,154,067 A    10/1964   Stenstrom et al.
3,771,355 A    11/1973   Sachs
               (Continued)

FOREIGN PATENT DOCUMENTS

AU       3443295 A    5/1996
CA       2324602 A    9/1999
               (Continued)

OTHER PUBLICATIONS

Li et al., "In Vivo Breast Sound-Speed Imaging with Ultrasound Tomography", Ultrasound in Med & Bioi., vol. 35, No. 10, 2009, pp. 1615-1628.
(Continued)

*Primary Examiner* — Joel F Brutus
(74) *Attorney, Agent, or Firm* — Wilson Sonsini Goodrich & Rosati (57) ABSTRACT

A method and system for generating an enhanced image of a volume of tissue, comprising: emitting acoustic waveforms toward the volume of tissue; detecting acoustic signals derived from acoustic waveforms interacting with the volume of tissue; generating a reflection rendering of a region of the volume of tissue; generating at least one of a sound speed map and an attenuation map of the region of the volume of tissue; generating a transfer map derived from a set of sound speed parameter values of the sound speed map and/or a set of acoustic attenuation parameter values of the acoustic attenuation map, the set of sound speed parameter values and the set of acoustic attenuation parameters associated with the set of elements of the region of the volume of tissue; and rendering an enhanced image of the volume of tissue, derived from processing of the reflection rendering with the transfer map.

20 Claims, 7 Drawing Sheets

(51) Int. Cl.
 *A61B 8/14* (2006.01)
 *A61B 8/15* (2006.01)
 *G06T 5/00* (2006.01)

(52) U.S. Cl.
 CPC ............... *A61B 8/15* (2013.01); *A61B 8/406* (2013.01); *A61B 8/4461* (2013.01); *A61B 8/4477* (2013.01); *A61B 8/4494* (2013.01); *A61B 8/483* (2013.01); *A61B 8/5246* (2013.01); *A61B 8/5253* (2013.01); *G06T 5/008* (2013.01); *G06T 2207/10136* (2013.01); *G06T 2207/30068* (2013.01)

(56) References Cited

U.S. PATENT DOCUMENTS

| | | |
|---|---|---|
| 3,881,466 A | 5/1975 | Wilcox |
| 3,886,489 A | 5/1975 | Jones |
| 3,925,610 A | 12/1975 | French et al. |
| 4,028,934 A | 6/1977 | Sollish |
| 4,059,010 A | 11/1977 | Sachs |
| 4,075,883 A | 2/1978 | Glover |
| 4,105,018 A | 8/1978 | Greenleaf et al. |
| 4,144,877 A | 3/1979 | Frei et al. |
| 4,222,274 A | 9/1980 | Johnson |
| 4,250,894 A | 2/1981 | Frei et al. |
| 4,317,369 A | 3/1982 | Johnson |
| 4,328,707 A | 5/1982 | Clement et al. |
| 4,363,326 A | 12/1982 | Kopel |
| 4,412,288 A | 10/1983 | Herman |
| 4,431,008 A | 2/1984 | Wanner et al. |
| 4,433,690 A | 2/1984 | Green et al. |
| 4,481,948 A | 11/1984 | Sole |
| 4,509,368 A | 4/1985 | Whiting et al. |
| 4,515,165 A | 5/1985 | Carroll |
| 4,541,436 A | 9/1985 | Hassler et al. |
| 4,542,744 A | 9/1985 | Barnes et al. |
| 4,562,540 A | 12/1985 | Devaney |
| 4,564,019 A | 1/1986 | Miwa |
| 4,606,342 A | 8/1986 | Zamba et al. |
| 4,646,756 A | 3/1987 | Watmough et al. |
| 4,662,222 A | 5/1987 | Johnson |
| 4,671,256 A | 6/1987 | Lemelson |
| 4,722,056 A | 1/1988 | Roberts et al. |
| 4,733,562 A | 3/1988 | Saugeon |
| 4,855,911 A | 8/1989 | Lele et al. |
| 4,858,124 A | 8/1989 | Lizzi et al. |
| 4,917,096 A | 4/1990 | Englehart et al. |
| 4,932,414 A | 6/1990 | Coleman et al. |
| 4,941,474 A | 7/1990 | Pratt, Jr. |
| 5,003,979 A | 4/1991 | Merickel et al. |
| 5,025,792 A | 6/1991 | Hon et al. |
| 5,029,476 A | 7/1991 | Metala et al. |
| RE33,672 E | 8/1991 | Miwa |
| 5,095,909 A | 3/1992 | Nakayama et al. |
| 5,103,129 A | 4/1992 | Slayton et al. |
| 5,143,069 A | 9/1992 | Kwon et al. |
| 5,158,071 A | 10/1992 | Umemura et al. |
| 5,158,536 A | 10/1992 | Sekins et al. |
| 5,178,147 A | 1/1993 | Ophir et al. |
| 5,179,455 A | 1/1993 | Garlick |
| 5,212,571 A | 5/1993 | Garlick et al. |
| 5,255,683 A | 10/1993 | Monaghan |
| 5,260,871 A | 11/1993 | Goldberg |
| 5,267,566 A | 12/1993 | Choucair et al. |
| 5,268,876 A | 12/1993 | Rachlin |
| 5,269,309 A | 12/1993 | Fort et al. |
| 5,280,788 A | 1/1994 | Janes et al. |
| 5,296,910 A | 3/1994 | Cole |
| 5,297,553 A | 3/1994 | Sliwa et al. |
| 5,304,173 A | 4/1994 | Kittrell et al. |
| 5,305,752 A | 4/1994 | Spivey et al. |
| 5,318,028 A | 6/1994 | Mitchell et al. |
| 5,329,817 A | 7/1994 | Garlick et al. |
| 5,339,282 A | 8/1994 | Kuhn et al. |
| 5,349,954 A | 9/1994 | Tiemann et al. |
| 5,372,138 A | 12/1994 | Crowley et al. |
| 5,394,875 A | 3/1995 | Lewis et al. |
| 5,398,691 A | 3/1995 | Martin et al. |
| 5,413,108 A | 5/1995 | Alfano |
| 5,415,164 A | 5/1995 | Faupel et al. |
| 5,421,338 A | 6/1995 | Crowley et al. |
| 5,433,202 A | 7/1995 | Mitchell et al. |
| 5,463,548 A | 10/1995 | Asada et al. |
| 5,465,722 A | 11/1995 | Fort et al. |
| 5,474,072 A | 12/1995 | Shmulewitz |
| 5,479,927 A | 1/1996 | Shmulewitz |
| 5,485,839 A | 1/1996 | Aida et al. |
| 5,487,387 A | 1/1996 | Trahey et al. |
| 5,492,126 A | 2/1996 | Hennige et al. |
| 5,501,655 A | 3/1996 | Rolt et al. |
| 5,513,639 A | 5/1996 | Satomi et al. |
| 5,524,630 A | 6/1996 | Crowley |
| 5,546,945 A | 8/1996 | Soldner |
| 5,548,658 A | 8/1996 | Ring et al. |
| 5,553,618 A | 9/1996 | Suzuki et al. |
| 5,558,092 A | 9/1996 | Unger et al. |
| 5,573,497 A | 11/1996 | Chapelon |
| 5,582,173 A | 12/1996 | Li |
| 5,588,032 A | 12/1996 | Johnson et al. |
| 5,588,430 A | 12/1996 | Bova et al. |
| 5,590,653 A | 1/1997 | Aida et al. |
| 5,590,657 A | 1/1997 | Cain et al. |
| 5,596,992 A | 1/1997 | Haaland et al. |
| 5,606,971 A | 3/1997 | Sarvazyan |
| 5,609,152 A | 3/1997 | Pellegrino et al. |
| 5,620,479 A | 4/1997 | Diederich |
| 5,640,956 A | 6/1997 | Getzinger et al. |
| 5,643,179 A | 7/1997 | Fujimoto |
| 5,660,185 A | 8/1997 | Shmulewitz et al. |
| 5,664,573 A | 9/1997 | Shmulewitz |
| 5,673,698 A | 10/1997 | Okada et al. |
| 5,678,565 A | 10/1997 | Sarvazyan |
| 5,715,825 A | 2/1998 | Crowley |
| 5,722,411 A | 3/1998 | Suzuki et al. |
| 5,743,863 A | 4/1998 | Chapelon |
| 5,749,364 A | 5/1998 | Sliwa, Jr. et al. |
| 5,759,162 A | 6/1998 | Oppelt et al. |
| 5,762,066 A | 6/1998 | Law et al. |
| 5,766,129 A | 6/1998 | Mochizuki |
| 5,785,663 A | 7/1998 | Sarvazyan |
| 5,787,049 A | 7/1998 | Bates |
| 5,797,849 A | 8/1998 | Vesely et al. |
| 5,800,350 A | 9/1998 | Coppleson et al. |
| 5,810,731 A | 9/1998 | Sarvazyan et al. |
| 5,817,025 A | 10/1998 | Alekseev et al. |
| 5,830,133 A | 11/1998 | Osten et al. |
| 5,833,614 A | 11/1998 | Dodd et al. |
| 5,833,627 A | 11/1998 | Shmulewitz et al. |
| 5,833,633 A | 11/1998 | Sarvazyan |
| 5,833,634 A | 11/1998 | Laird et al. |
| 5,836,882 A | 11/1998 | Frazin |
| 5,836,894 A | 11/1998 | Sarvazyan |
| 5,846,202 A | 12/1998 | Ramamurthy et al. |
| 5,851,182 A | 12/1998 | Sahadevan |
| 5,855,554 A | 1/1999 | Schneider et al. |
| 5,865,167 A | 2/1999 | Godik |
| 5,865,743 A | 2/1999 | Godik |
| 5,891,619 A | 4/1999 | Zakim et al. |
| 5,945,674 A | 8/1999 | Dukor |
| 6,002,958 A | 12/1999 | Godik |
| 6,005,916 A | 12/1999 | Johnson et al. |
| 6,014,473 A | 1/2000 | Hossack et al. |
| 6,023,632 A | 2/2000 | Wilk |
| 6,050,943 A | 4/2000 | Slayton et al. |
| 6,056,690 A | 5/2000 | Roberts |
| 6,078,677 A | 6/2000 | Dolleman et al. |
| 6,083,166 A | 7/2000 | Holdaway et al. |
| 6,102,857 A | 8/2000 | Kruger |
| 6,109,270 A | 8/2000 | Mah et al. |
| 6,117,080 A | 9/2000 | Schwartz |
| 6,135,960 A | 10/2000 | Holmberg |
| 6,146,897 A | 11/2000 | Cohenford et al. |
| 6,149,441 A | 11/2000 | Pellegrino et al. |

(56) References Cited

U.S. PATENT DOCUMENTS

| | | |
|---|---|---|
| 6,165,734 A | 12/2000 | Garini et al. |
| 6,190,334 B1 | 2/2001 | Lasky et al. |
| 6,235,038 B1 | 5/2001 | Hunter et al. |
| 6,242,472 B1 | 6/2001 | Sekins et al. |
| 6,245,017 B1 | 6/2001 | Hashimoto et al. |
| 6,256,090 B1 | 7/2001 | Chen et al. |
| 6,289,235 B1 | 9/2001 | Webber et al. |
| 6,292,682 B1 | 9/2001 | Kruger |
| 6,296,489 B1 | 10/2001 | Blass et al. |
| 6,317,617 B1 | 11/2001 | Gilhuijs et al. |
| 6,351,660 B1 | 2/2002 | Burke et al. |
| 6,368,275 B1 | 4/2002 | Sliwa et al. |
| 6,385,474 B1 | 5/2002 | Rather et al. |
| 6,413,219 B1 | 7/2002 | Avila et al. |
| 6,425,869 B1 | 7/2002 | Rafter et al. |
| 6,428,477 B1 | 8/2002 | Mason |
| 6,450,960 B1 | 9/2002 | Rather et al. |
| 6,451,013 B1 | 9/2002 | Bays et al. |
| 6,475,150 B2 | 11/2002 | Haddad |
| 6,478,739 B1 | 11/2002 | Hong |
| 6,490,469 B2 | 12/2002 | Candy |
| 6,511,427 B1 | 1/2003 | Sliwa, Jr. et al. |
| 6,527,759 B1 | 3/2003 | Tachibana et al. |
| 6,540,678 B2 | 4/2003 | Rather et al. |
| 6,559,178 B1 | 5/2003 | Zamoyski |
| 6,574,499 B1 | 6/2003 | Dines et al. |
| 6,587,540 B1 | 7/2003 | Johnson et al. |
| 6,612,988 B2 | 9/2003 | Maor et al. |
| 6,636,584 B2 | 10/2003 | Johnson et al. |
| 6,645,202 B1 | 11/2003 | Pless et al. |
| 6,672,165 B2 | 1/2004 | Rather et al. |
| 6,716,412 B2 | 4/2004 | Unger |
| 6,728,567 B2 | 4/2004 | Rather et al. |
| 6,776,760 B2 | 8/2004 | Marmarelis |
| 6,785,570 B2 | 8/2004 | Nir |
| 6,810,278 B2 | 10/2004 | Webber et al. |
| 6,837,854 B2 | 1/2005 | Moore et al. |
| 6,883,194 B2 | 4/2005 | Corbeil et al. |
| 6,926,672 B2 | 8/2005 | Moore et al. |
| 6,939,301 B2 | 9/2005 | Abdelhak |
| 6,984,210 B2 | 1/2006 | Chambers et al. |
| 7,025,725 B2 | 4/2006 | Dione et al. |
| 7,179,449 B2 | 2/2007 | Lanza et al. |
| 7,285,092 B2 | 10/2007 | Duric et al. |
| 7,346,203 B2 | 3/2008 | Turek et al. |
| 7,497,830 B2 | 3/2009 | Li |
| 7,530,951 B2 | 5/2009 | Fehre et al. |
| 7,556,602 B2 | 7/2009 | Wang et al. |
| 7,570,742 B2 | 8/2009 | Johnson et al. |
| 8,663,113 B2 | 3/2014 | Schmidt et al. |
| 2001/0029334 A1 | 10/2001 | Graumann et al. |
| 2001/0037075 A1 | 11/2001 | Candy |
| 2001/0051774 A1 | 12/2001 | Littrup et al. |
| 2002/0065466 A1 | 5/2002 | Rather et al. |
| 2002/0099290 A1 | 7/2002 | Haddad |
| 2002/0120196 A1 | 8/2002 | Dubberstein et al. |
| 2002/0131551 A1 | 9/2002 | Johnson et al. |
| 2003/0138053 A1 | 7/2003 | Candy et al. |
| 2004/0030227 A1 | 2/2004 | Littrup et al. |
| 2004/0059265 A1 | 3/2004 | Candy et al. |
| 2004/0122325 A1 | 6/2004 | Chambers et al. |
| 2004/0152986 A1 | 8/2004 | Fidel et al. |
| 2004/0167396 A1 | 8/2004 | Chambers et al. |
| 2004/0181154 A1 | 9/2004 | Peterson et al. |
| 2005/0165309 A1 | 7/2005 | Varghese et al. |
| 2005/0196025 A1 | 9/2005 | Schofield |
| 2005/0260745 A1 | 11/2005 | Domansky et al. |
| 2006/0009693 A1 | 1/2006 | Hanover et al. |
| 2006/0020205 A1 | 1/2006 | Kamiyama |
| 2006/0064014 A1 | 3/2006 | Falco et al. |
| 2006/0084859 A1 | 4/2006 | Johnson et al. |
| 2006/0085049 A1 | 4/2006 | Cory et al. |
| 2006/0287596 A1 | 12/2006 | Johnson et al. |
| 2006/0293597 A1 | 12/2006 | Johnson et al. |
| 2007/0015949 A1 | 1/2007 | Kaiser |
| 2007/0167823 A1 | 7/2007 | Lee et al. |
| 2007/0282200 A1 | 12/2007 | Johnson et al. |
| 2008/0045864 A1 | 2/2008 | Candy et al. |
| 2008/0058682 A1 | 3/2008 | Azhari et al. |
| 2008/0218743 A1 | 9/2008 | Stetten et al. |
| 2008/0229832 A1 | 9/2008 | Huang et al. |
| 2008/0269812 A1 | 10/2008 | Gerber et al. |
| 2008/0275344 A1 | 11/2008 | Glide-Hurst et al. |
| 2008/0281205 A1 | 11/2008 | Naghavi et al. |
| 2008/0294027 A1 | 11/2008 | Frinking et al. |
| 2008/0294043 A1 | 11/2008 | Johnson et al. |
| 2008/0319318 A1 | 12/2008 | Johnson et al. |
| 2009/0035218 A1 | 2/2009 | Ross et al. |
| 2009/0076379 A1 | 3/2009 | Hamill et al. |
| 2009/0129556 A1 | 5/2009 | Ahn |
| 2009/0143674 A1 | 6/2009 | Nields et al. |
| 2010/0286522 A1* | 11/2010 | Beach ................ A61B 5/02007 600/441 |
| 2010/0331699 A1 | 12/2010 | Yu et al. |
| 2011/0152685 A1 | 6/2011 | Misono |
| 2011/0201932 A1 | 8/2011 | Duric et al. |
| 2013/0041260 A1* | 2/2013 | Schmidt ............... A61B 8/0825 600/442 |
| 2013/0041261 A1 | 2/2013 | Li et al. |
| 2013/0267850 A1 | 10/2013 | Berman |
| 2014/0316269 A1 | 10/2014 | Zhang et al. |

FOREIGN PATENT DOCUMENTS

| | | |
|---|---|---|
| EP | 0097917 A | 1/1984 |
| EP | 284055 A | 9/1988 |
| EP | 317049 A | 5/1989 |
| EP | 320444 A | 6/1989 |
| EP | 351610 A | 1/1990 |
| EP | 538241 A | 4/1993 |
| EP | 0609922 A | 8/1994 |
| EP | 614651 A | 9/1994 |
| EP | 642762 A | 3/1995 |
| EP | 661029 A | 7/1995 |
| EP | 774276 A | 5/1997 |
| EP | 1063920 A | 1/2001 |
| GB | 2040642 A | 8/1980 |
| JP | 2005253827 A | 9/2005 |
| JP | 2007181679 A | 7/2007 |
| JP | 2009034521 A | 2/2009 |
| WO | 9947046 A | 9/1999 |
| WO | 199947046 | 9/1999 |
| WO | 0230288 A | 4/2002 |
| WO | 2002028350 | 4/2002 |
| WO | 2004061743 A | 7/2004 |
| WO | 2005057467 A | 6/2005 |
| WO | 2007023408 A | 3/2007 |

OTHER PUBLICATIONS

Li et al., Breast Imaging Using Transmission Ultrasound: Reconstructing Tissue Parameters of Sound Speed and Attenuation, 2008 International Conference on BioMedical Engineering and Informatics, IEEE computer society, 708-712.

Li et al., Comparison of ultrasound attenuation tomography methods for breast imaging, Medical Imaging 2008: UltrasonicImaging and Signal Processing, Proc. of SPIE vol. 6920, 692015-(1-9), 2008.

Li et al., Refraction corrected transmission ultrasound computed tomography for application in breast imaging, Med. Phys. 37(5), May 2010, 2233-2246.

Louvar et al., "Correlation of Color Doppler Flow in the Prostate with Tissue Microvascularity," Cancer 1:83(1) (1998) 135-40.

Marias, "Automatic Labelling and BI-RADS Characterisation of Mammogram Densities," Proc 2005 IEEE, Sep. 1-4, 2005, pp. 6394-6398.

Mast, "Empirical Relationships Between Acoustic Parameters in Human Soft Tissues," Acoust Research Letters Online, Nov. 16, 2000, pp. 37-42.

Masugata et al., "Relationship Between Myocardial Tissue Density Measured by Microgravimetry and Sound Speed Measured by Acoustic Microscopy," Ultrasound in Med & Biol 25(9) (1999) 1459-1463.

(56) References Cited

OTHER PUBLICATIONS

McCormick et al., Multigrid solution of a linearized, regularized least-squares problem in electrical impedance tomography, Inverse Problems 9, 1993, 697-713.
Metz, "Basic principles of ROC analysis"; Semin Nucl Med. Oct. 8, 1978 (4):283-98.
Metz, "Receiver Operating Characteristic Analysis: A Tool for the Quantitative Evaluation of Observer Performance and Imaging Systems"; J Am Coli Radiol 2006; 3: 413-422.
Metz, "ROC methodology in radiologic imaging"; Invest Radiol. Sep. 21, 1986 (9):720-33.
Miller et al., "Sonoporation of Cultured Cells in the Rotating Tube Exposure System," Ultrasound Med & Biol 25 (1999) 143-149.
Mitchell, An Introduction to Genetic Algorithms, pp. 8-11, 35-78, 155-179 (MIT Press, 1996).
Nelson et al., "Interactive Acquisition, Analysis and Visualization of Sonographic Volume Data," International J Imaging Sys and Tech 8(26) (1997) 26-37.
Noble et al., "Spleen Hemostasis Using High-Intensity Ultrasound: Survival and Healing," J. Trauma Injury, Infection, and Critical Care 53(6) (2002) 1115-1120.
Oh et al., Multigrid Tomographic Inversion With Variable Resolution Data and Image Spaces, IEEE Transactions on Image Proessing, vol. 15, No. 9, Sep. 2006.
Ophir et al., "Elastography: Ultrasonic Estimation and Imaging of the Elastic Properties of Tissues," Proc Instn Mech Engrs 213(Part H) (1999) 203-233.
Palomares et al., "Mammographic Density Correlation with Gail Model Breast Cancer Risk Estimates and Component Risk Factors," Cancer Epidemiol Biomarkers Prev 15(7) (2006) 1324-1330.
Quan et al., Sound-speed tomography using first-arrival transmission ultrasound for a ring array, Medical Imaging 2007: Ultrasonic Imaging and Signal Processing, Proc. of SPIE vol. 6513.
Robinson et al., "Quantitative Sonography," Ultrasound in Med & Biol 12(7): 555-65 (1986).
Schmidt et al., "Modification of Kirchhoff migration with variable sound speed and attenuation for tomographic imaging of the breast," Proc. of SPIE vol. 7968, Mar. 25, 2011.
Sehgal et al., "Visualization of Breast Calcification by Acoustic Resonance Imaging," Radiology Supplement, 84th Scientific Assembly and Annual Meeting, Nov. 29-Dec. 4, 1998 presented in McCormick Place, Chicago, Illinois, vol. 209, listing: 1150 (1998).
Shi et al., "Effects of Pressure Changes on Harmonic and Subharmonic Response of US Contrast Microbubbles," 84th Scientific Assembly and Annual Meeting, Nov. 29-Dec. 4, 1998, presented in McCormick Place, Chicago, Illinois, vol. 209, listing: 1154 (1998).
Singh, Seema et al. "Color Doppler Ultrasound as an Objective Assessment Tool for Chemotherapeutic Response in Advanced Breast Cancer." Breast Cancer, 2005, vol. 12, No. 1, 2005, pp. 45-51.
Teubner et al., "Comparative Studies of Various Echomammography," Ultraschall in Der Medizin 3(3) (1982) 109-18, G. Thieme Verlag, Stuttgart/New York.
Vaezy et al., "Real-Time Visualization of High-Intensity Focused Ultrasound Treatment Using Ultrasound Imaging," Ultrasound in Med & Biol 27(1) (2001) 33-42.
Walach et al., Local Tissue Attenuation Images Based on Pulsed-Echo Ultrasound Scans, IEEE Transactions Onbiomedical Engineering, vol. 36. No. 2, Feb. 1989.
Wei et al., "Correlation Between Mammographic Density and Volumetric Fibroglandular Tissue Estimated on Breast MR Images," Med Phys 31(4) (2004) 933-942.
Weiwad et al., "Direct Measurement of Sound Velocity in Various Specimens of Breast Tissue," Invest Radiol 35(12) (2000) 721-6.
Wiskin et al., "Full Inverse Scattering vs. Born-like Approximation for Imaging in a Stratified Ocean," Proc. Eng. in Harmony with the Ocean, (Oceans '93), Victoria, British Columbia (Oct. 1993).
Wolfe, "Risk for Breast Cancer Development Determined by Mammographic Parenchymal Pattern," Cancer 37(5) (1976) 2486-2493.
Xu, et al. "A Study of 3-Way Image Fusion for Characterizing Acoustic Properties of Breast Tissue." Medical Imaging 2008: Ultrasonic Imaging and Signal Processing. Feb. 16, 2008.
Yaffe, "Breast Cancer Risk and Measured Mammographic Density," Eur J Cancer Prevention 7(1) (1998) S47-55.
Yaman, C. et al., "Three-Dimensional Ultrasound to Assess the Response to Treatment in Gynecological Malignancies." Gynecologic Oncology, Academic Press, vol. 97, No. 2, May 1, 2005, pp. 665-668.
Yankelevitz et al., "Small Pulmonary Nodules: Volumetrically Determined Growth Rates Based on CT Evaluation," Radiology 217 (2000) 251-256.
Zhang et al., A comparison of material classification techniques for ultrasound inverse imaging, J. Acoust. Soc. Am. 111 (1), Pt. 1, Jan. 2002.
Andre et al., "A New Consideration of Diffraction Computed Tomography for Breast Imaging: Studies in Phantoms Patients," Acoustical Imaging, 21, 379 (1995).
Azhari et al., "Volumetric Imaging with Ultrasonic Spiral CT," Radiol 212 (1999) 270-275.
Banihashemi, B. et al., "Ultrasound Imaging of Apoptosis in Tumor Response: Novel Preclinical Monitoring of Photodynamic Therapy Effects." Cancer Research, vol. 68, No. 20, Oct. 15, 2008, pp. 8590-8596.
Barlow et al., "Prospective Breast Cancer Risk Prediction Model for Women Undergoing Screening Mammogrpahy," J. Nat'l Cancer Institute 98(17): 1204-1214 (2006).
Boone et al., "Dedicated Breast CT: Radiation Dose and Image Quality Evaluation," Med Phys 221(3): 657-667 (2001).
Borup et al., "Nonperturbative Diffraction Tomography via Gauss-Newton Iteration Applied to the Scattering Integral Equation," Ultrasonic Imaging 1, Academic Press, Inc. (1992) 69-85.
Boston et al., "Estimation of the Content of Fat and Parenchyma in Breast Tissue Using MRI T1 Histograms and Phantoms," MRI 23: 591-599 (2005).
Boyd, "Quantitative Classification of Mammographic Densities and Breast Cancer Risk: Results from the Canadian National Breast Screening Study," J Nat'l Cancer Institute 87(9): 670-675 (1995).
Byng et al., The Quantitative Analysis of Mammographic Densities,: Phys Med Biol 39 (1994) 1629-1638.
Cadzow, "Signal enhancement—A composite property mapping algorithm," IEEE Transactions on Acoustics, Speech and Signal Processing 36(1) (1988) 49-62.
Candy et al., "Signal Processing: The Model-Based Approach," pp. 178-213 (McGraw Hill, 1986).
Centerline, PortalVision section, Summer 2002 edition, published by Varian Medical Systems.
Chan et al., An Agglomeration Multigrid Method for Unstructured Grids, Contemporary Mathematics, vol. 218, 1998.
Chang et al., "Breast Density Analysis in 3-D Whole Breast Ultrasound Images," IEEE Proc 28th IEEE EMBS Annual International Conference (2006) 2795-2798.
Chang et al., Kirchhoff migration of ultrasonic images, Materials evaluation, V59, N3, 413-417, 2001.
Chelfouh et al., "Characterization of Urinary Calculi: in Vitro Study of 'Twinking Artifact' revealed by Color-Flow Sonography," AJR Am. J. Roentgenol. 171( 4) (1998) 1055-60.
Chen et al., "Projecting Absolute Invasive Breast Cancer Risk in White Women with a Model that Includes Mammographic Density," J. Nat'l Cancer Institute 98(17) (2006) 1215-1226.
Dean, "The Radon Transform and Some of Its Applications," Krieger Publishing Company, Malabar, Florida (1993).
Diederich et al., "The design of ultrasound applicators for interstitial hyperthermia," Ultrasonics Symposium, Proc IEEE 1993 Baltimore, MD, USA Oct. 31-Nov. 3, 1993, New York, NY, USA, 1215-1219.
Drineas et al., "Distance matrix reconstruction from incomplete distance information for sensor network localization," 3rd Annual IEEE Communications Society on Sensor and Ad Hoc Communications and Networks, Sep. 2006, pp. 536-544.
Duric et al. "Computed Ultrasound Risk Evaluation," Barbara Ann Karmanos Cancer Institute. pp. 1-23. 2008.

(56) References Cited

OTHER PUBLICATIONS

Duric et al., "Detection of Breast Cancer with Ultrasound Tomography: First Results with the Computed Ultrasound Risk Evaluation (CURE) Prototype," Med Phys 34(2) (2007).
Dussik, "The Ultrasonic Field as a Medical Tool," Amer J Phys Med 33(1) (1954) 5-20.
Fjield et al., "A Parametric Study of the Concentric-Ring Transducer Design for MRI Guided Ultrasound Surgery," J. Acoust. Soc. America 100 (2) Pt. 1 (1996).
Gervias et al., "Renal Cell Carcinoma: Clinical Experience and Technical Success with Radio-frequency Ablation of 42 Tumors," Radiology 226 (2003) 417-424.
Glide et al., "Novel Approach to Evaluating Breast Density Utilizing Ultrasound Tomography," Med Phys 34(2) (2007) 744-753.
Glide, "A Novel Approach to Evaluating Breast Density Using Ultrasound Tomography," Dissertation Graduate School of Wayne State University (2007).
Glide-Hurst et al., "A Novel Ultrasonic Method for Measuring Breast Density and Breast Cancer Risk," Med Imaging 2008, Proc SPIE vol. 6920, 69200Q.
Glide-Hurst et al., "Volumetric breast density evaluation from ultrasound tomography images", Medical Physics, vol. 35, 2008, pp. 3988-3997.
Glide-Hurst, "A New Method for Quantitative Analysis of Mammographic Density," Med Phys 34(11) (2007) 4491-4498.
Greenleaf et al., "Multidimensional Visualization of Ultrasonic Images," J Acoust Soc Amer 95 (1994) 2902.
Greenleaf et al., "Artificial Cavitation Nuclei Significantly Enhance Acoustically Incuded Cell Transfection," Ultrasound Med & Biol 24 (1998) 587-595.
Greenleaf et al., "Introduction to Computer Ultrasound Tomography," Computer Aided Tomography and Ultrasonics in Medicine, (1970) North-Holland 125-136.
Greenleaf, "Computerized Tomography with Ultrasound," Proc IEEE 71(3) (1983) 330-337.
Greenleaf, "Tissue Characterization with Ultrasound: vol. II: Results and Applications," CRC Press, Inc., Boca Raton, Florida, pp. 95-122.

Harmuth, "Sequency Theory: Foundations and Applications, Advances in Electronics and Electron Physics," (Academic Press, 1977) 18-95.
Hayashi, "A New Method of Measuring in Vivo Sound Speed in the Reflection Mode," J Clin Ultrasound 16(2) (1988) 87-93.
Haykin, "Neural Networks—A Comprehensive Foundation," Prentice Hall (1998) 236-284.
Hebden et al., "Acoustically Modulated Electrical Impedance Tomography, "Proc SPIE 1231 (1990) 7-14.
Jellins et al., "Velocity Compensation in Water-Coupled Breast Echography," Ultrasonics 11(5) (1973) 223-6.
Jellins, "Breast Tissue Characterization" Tissue Characterization with Ultrasound 2 (1986) CRC Press 95-122.
Johnson et al., "Comparison of Inverse Scattering and Other Tomographic Imaging Algorithms Using Simulated and Tank Data for Modeling Subbottom Imaging Systems," IEEE Oceans '93 Symposium, Nov. 1993, vol. 1 (1993) 458-492.
Johnson et al., "Modeling of Inverse Scattering and Other Tomographic Algorithms in Conjunction with Wide Bandwidth Acoustic Transducer Arrays for Towed or Autonomous Sub-bottom Imaging Systems," Proc. Mastering the Oceans Through Technology, Oceans Newport, Rhode Island, USA, Oct. 26-29, 1992 294-299.
Kaizer et al., "Ultrasonographically Defined Parenchymal Pattenrs of the Breast: Relationship to Mammographic Patterns and Other Risk Factors for Breast Cancer," Brit J Radiology 61(722) (1988) 118-24.
Karssemeijer, "Automated Classification of Parenchymal Patterns in Mammograms," Phys Med Biol 43 (1998) 365-378.
Kerlikowske et al., "Longitudinal Measurement of Clinical Mammographic Breast Density to Improve Estimation of Breast Cancer Risk," J. Nat'l Cancer Institute 99(5) (2007) 386-395.
Klimes, Grid Travel-time Tracing: Second-order Method for the First Arrivals in Smooth Media, PAGEOPH, vol. 148, Nos. 3/4, 1996.
Knapp et al., "The generalized correlation method for estimation of time delay," IEEE Transactions on Acoustics, Speech and Signal Processing 24(4) (1976) 320-327.
Kossoff et al., "Average Velocity of Ultrasound in the Human Female Breast," J Acoust Soc America 53(6) (1973) 1730-6.
Li et al., "Clinical Breast Imaging Using Sound-Speed Reconstructions of Ultrasound Tomography Data," Med Imaging 2008, Proc SPIE vol. 6920, 6920009.

\* cited by examiner

METHOD FOR GENERATING AN ENHANCED IMAGE OF A VOLUME OF TISSUE

CROSS-REFERENCE TO RELATED APPLICATIONS

This application claims the benefit of U.S. Provisional Application Ser. No. 62/033,265 filed 5 Aug. 2014, which is incorporated in its entirety herein by this reference.

TECHNICAL FIELD

This invention relates generally to the medical imaging field, and more specifically to an improved method for generating an enhanced image of a volume of tissue in the ultrasound medical imaging field.

BACKGROUND

Early detection of breast cancer and other types of cancer is typically an important factor in successful treatment. Ultrasound tomography is a promising imaging modality that has the potential to improve medical imaging of tissue for screening and diagnosis purposes compared to conventional imaging techniques. For instance, mammography is the current standard for breast screening, but involves ionizing radiation that precludes frequent imaging, and mammography has low sensitivity for detection of cancer in patients with dense breast tissue, which leads to a relatively high false negative rate. As another example, magnetic resonance imaging (MRI) is prohibitively expensive for routine and also has limited accessibility.

A basic principle of conventional ultrasound involves emitting an acoustic wave or beam along a focused path from a source transmitter, and allowing the wave to scatter (e.g., in reflection, refraction, diffraction, transmission) from tissue or other boundaries in its path. The scattered wave returns to a surface of one or more receiving elements, which can be centered around and/or include the transmitter(s). The time of translation can be converted into a depth distance by multiplying the time by a speed of sound in the media. The received signal is output to a graphical display for user interpretation. However, current methods of ultrasonic imaging have some drawbacks and limitations. For instance, methods of generating an image can produce outputs that do not match regulatory guidelines (e.g., guidelines of the U.S. Food and Drug Administration) and/or obscure target objects in a field of view, thus making analysis of such images difficult. Furthermore, current ultrasound systems and methods are typically configured to accommodate a small imaging region, resulting in difficulties in imaging entire organs, such as the breast. Furthermore, the performance of ultrasound scanning is dependent on the skills of the operator and image quality can vary from user to user.

Thus, there is a need in the ultrasound imaging field to create an improved method for generating an enhanced image of a volume of tissue. This invention provides such an improved method for generating an enhanced image of a volume of tissue.

DESCRIPTION OF THE PREFERRED EMBODIMENTS

The following description of preferred embodiments of the invention is not intended to limit the invention to these preferred embodiments, but rather to enable any person skilled in the art to make and use this invention.

1. Method

Figure 1:
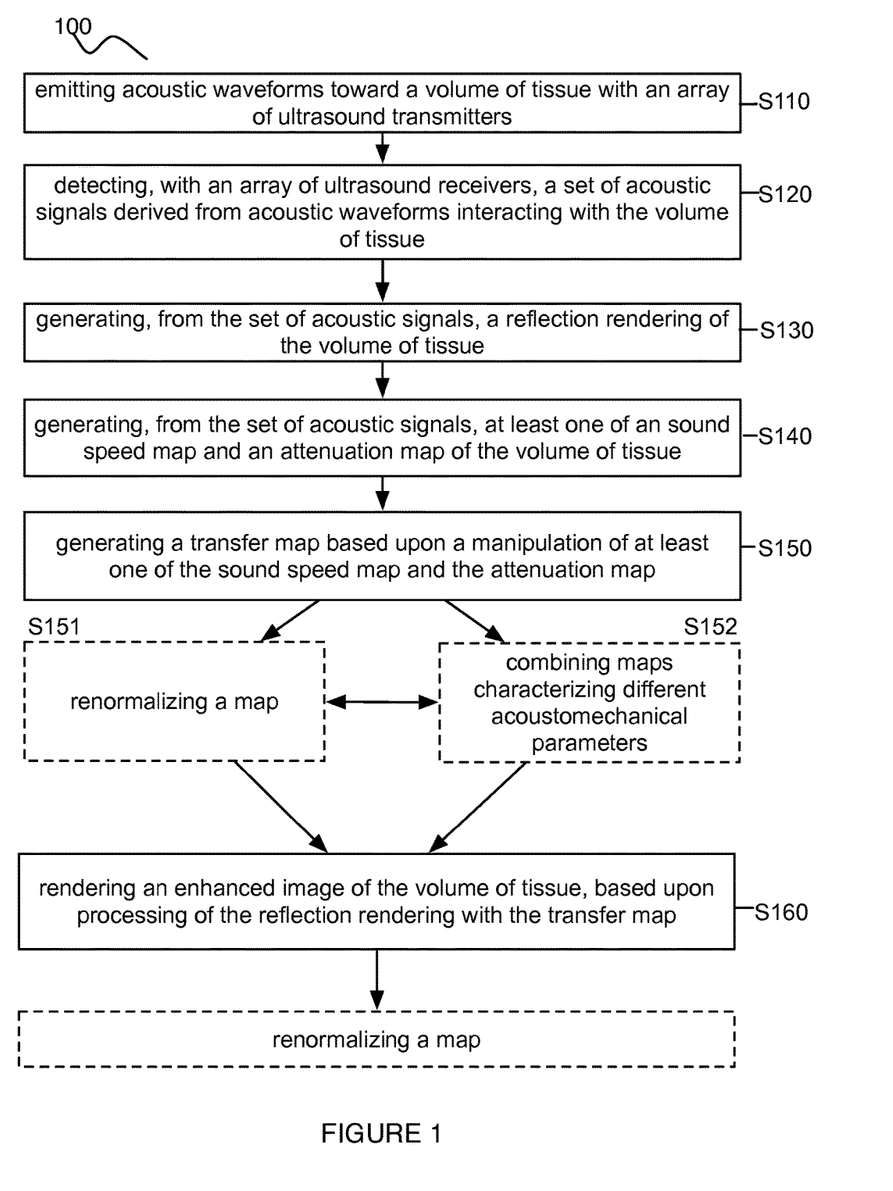
FIG. 1 is a schematic of a method of generating an enhanced image of a volume of tissue.

In one embodiment, as shown in FIG. 1, a method 100 for generating an enhanced image of a volume of tissue includes: emitting acoustic waveforms toward the volume of tissue with an array of ultrasound transmitters S110; detecting, with an array of ultrasound receivers, a set of acoustic signals S120 derived from acoustic waveforms interacting with the volume of tissue; generating, from the set of acoustic signals, a reflection rendering of the volume of tissue S130; generating, from the set of acoustic signals, at least one of an acoustic speed rendering and an acoustic attenuation rendering of the volume of tissue S140; generating a transfer map based upon a manipulation of at least one of the acoustic speed rendering and the acoustic attenuation rendering S150; and rendering an enhanced image of the volume of tissue, based upon processing of the reflection rendering with the transfer map S160.

The method 100 functions to render ultrasound images that enhance target objects within a field of view, in order to facilitate characterization of the volume of tissue (e.g., a whole breast, another organ). Additionally or alternatively, the method 100 can function to produce images that are aligned with regulatory standards for medical imaging, as regulated, for instance, by the U.S. Food and Drug Administration (FDA). The method 100 is preferably used to characterize tissue of a human breast, but can additionally or alternatively be used to characterize tissue of an arm, leg, other appendage, and/or any suitable volume of tissue in a human or other animal. In relation to current ultrasound methods and systems, the method 100 can improve sensitivity in detection of suspicious masses within acoustic reflection renderings, while providing specificity in characterization of types of masses. The method 100 can, however, function to enable diagnosis, monitoring, and/or characterization of a volume of tissue in any other suitable manner.

In one embodiment, the method is used to generate one or more renderings that can be used to detect abnormalities (e.g., cancerous tissues) in a human or other animal. As such, in one variation the method 100 can be used to characterize the tissue to facilitate diagnoses of cancer, assess its type and determine its extent (e.g., to determine whether a mass in the tissue is surgically removable), or to assess risk of cancer development (e.g., measuring breast tissue density). In yet another embodiment, the method 100 can be used to characterize and/or investigate particular aspects of the tissue, such as to determine whether a mass in the tissue is a tumor, cyst, fibroadenoma, or other kind of mass. However, the method 100 can be used in any suitable application for imaging a volume of tissue or other suitable object. The method 100 is preferably implemented, at least in part, by way of an embodiment, variation, and/or example of the system 200 described in Section 2 below; however, the method 100 can additionally or alternatively be implemented using any other suitable system.

Block S110 recites: emitting acoustic waveforms toward the volume of tissue with an array of ultrasound transmitters, and Block S120 recites: detecting, with an array of ultrasound receivers, a set of acoustic signals derived from acoustic waveforms interacting with the volume of tissue. Blocks S110 and S120 function to gather acoustic data from which renderings of the volume of tissue can be derived in other Blocks of the method 100. Emitting acoustic waveforms preferably includes surrounding the volume of tissue with the array of ultrasound transmitters, and more preferably with a ring transducer comprising the array of ultrasound transmitters. The acoustic waveforms can be characterized by frequencies of approximately 1-20 MHz, or any suitable frequency for medical imaging or other applications. The detected acoustic signals of Block S120 are preferably derived from interactions between the emitted acoustic waveforms of Block S110 and the tissue, wherein interactions can include one or more of: scattering (e.g., reflection, refraction, diffraction, diffusion, etc.) and transmission of the acoustic waves through the tissue. The acoustic signals can travel along a straight, bent, zig-zag, or curved path, or a path of any suitable shape as determined by the physics of acoustic wave propagation.

Figure 2A:
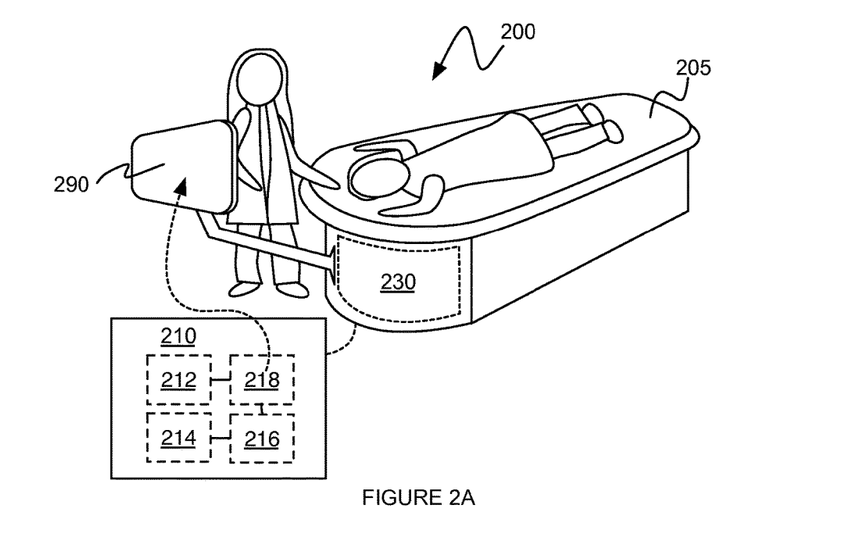
FIGS. 2A-2C are schematics of an embodiment of a system including an exemplary scanner and ring transducer, respectively, implementing at least a portion of a method of generating an enhanced image of a volume of tissue.

In Blocks S110 and S120, emitting acoustic waveforms and detecting a set of acoustic signals can be performed with an ultrasound tomographic scanner 200 and methods similar to those described in U.S. Pat. Nos. 6,385,474 and 8,663,113, and U.S. Publication Nos. 2011/0201932 and 2013/0041261, which are each incorporated in its entirety by this reference. However, any suitable ultrasound device or scanner may be used. As shown in FIG. 2A, the steps of scanning the tissue and detecting acoustic signals are preferably performed during a scan of a patient lying prone on their stomach on a scanner table 205 having an opening that provides access to the volume of tissue of the patient. The table, which may be made of a durable, flexible material such as sailcloth, preferably contours to the patient's body, thereby increasing scanning access to the axilla regions of the breast and increasing patient comfort. The opening in the table allows the breast (or other appendage) to protrude through the table and be submerged in an imaging tank 210 filled with water or another suitable fluid as an acoustic coupling medium that propagates acoustic waves.

Figure 2B:
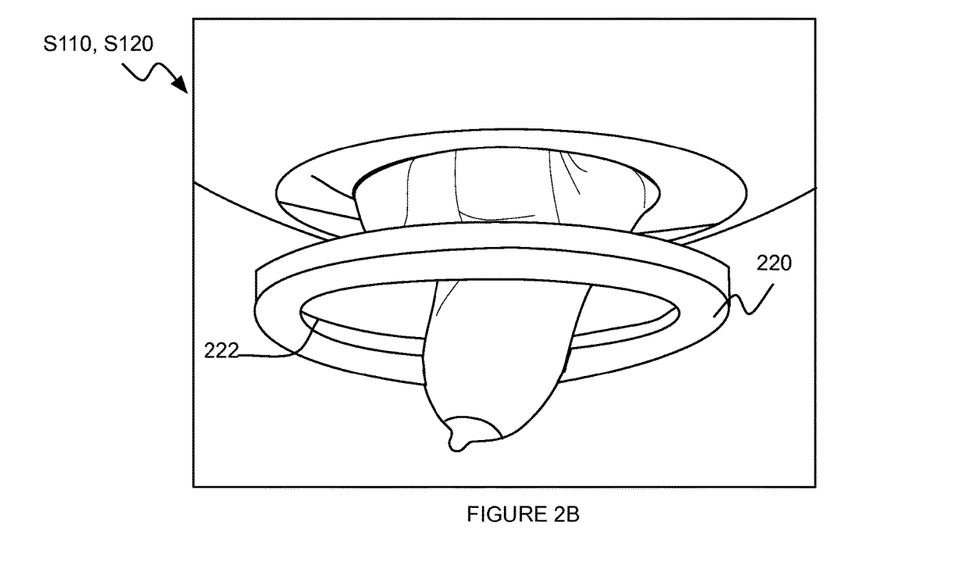
Figure 2C:
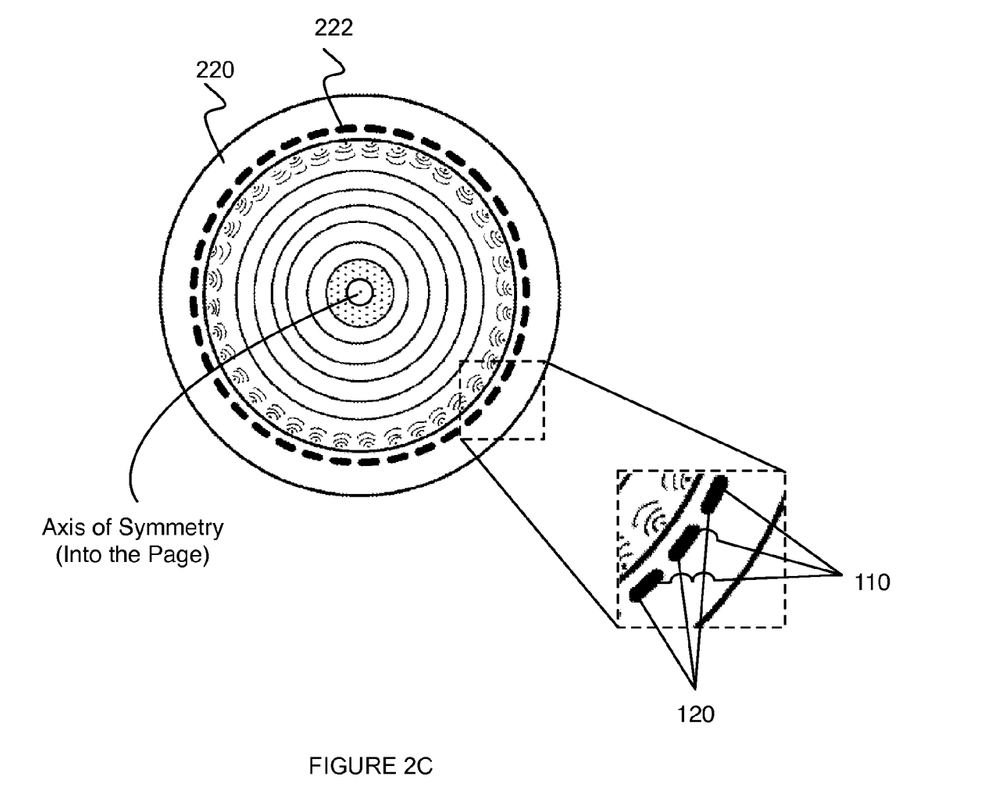

As shown in FIGS. 2B and 2C, a ring-shaped transducer 220 with transducer elements 222 can be located within the imaging tank and encircle or otherwise surround the breast, wherein the transducer elements 222 can comprise an array of ultrasound transmitters 110 and/or an array of ultrasound receivers 120. Multiple ultrasound transmitters no that direct safe, non-ionizing ultrasound pulses toward the tissue, and multiple ultrasound receivers 120 that receive and record acoustic signals scattering from the tissue and/or transmitted through the tissue, are distributed around the ring transducer 220, and in one configuration, can be organized such that each ultrasound transmitter element is paired with a corresponding ultrasound receiver element, each ultrasound transmitter element is surrounded by two adjacent ultrasound transmitter elements, each ultrasound receiver element is surrounded by two adjacent ultrasound receiver elements, and the transducer is axially symmetric, as in FIG. 2C.

During the scan, the ring transducer 220 moves to image all of the targeted tissue, such as in an anterior-posterior direction between the chest wall and the nipple region of the breast to acquire an acoustic data set including measurements such as acoustic reflection, acoustic attenuation, and sound speed, preferably at discrete scanning steps, or coronal "slices". The ring transducer 220 can be configured to scan step-wise in increments or travel continuously from the chest wall towards the nipple, and/or from the nipple towards the chest wall. However, the ring transducer 220 may additionally and/or alternatively receive data regarding any suitable biomechanical property of the tissue during the scan, and in any suitable direction.

In some embodiments, the scanner table can comprise an embodiment, variation, or example of the patient interface system described in U.S. application Ser. No. 14/208,181 entitled "Patient Interface System" and filed on 13 Mar. 2014, which is hereby incorporated in its entirety by this reference. Furthermore, in a specific example, Blocks S110 and/or S120 can implement a ring transducer 220 having 2048 transducer elements in cooperation with an ultrasound tomographic scanner 200 having 512 receive channels, 512 transmit channels, an operating frequency of 3 MHz, a data resolution of 14 bits, an image resolution of 0.7 mm, a slice thickness of 2.5 mm, a reconstruction time per slice of 15 seconds, and an ability to accommodate volumes of tissue 22 cm in diameter. In variations and examples, the ring transducer 220 can be the ring transducer of the ultrasound scanning system described in U.S. application Ser. No. 14/811,316. However, Blocks S110 and/or S120 can additionally or alternatively be implemented using any other suitable patient interface system.

Emitting and detecting in Blocks S110 and S120 are preferably performed in a rapid manner, such as with a data acquisition time of less than approximately 1 second per "slice", which may help to avoid motion artifacts in the subsequent morphology renderings and enables the use of contrast agents. However, any other suitable acquisition time can characterize emitting acoustic waveforms and/or detecting acoustic signals as in Blocks S110 and S120. The emitted waveforms and/or detected signals can additionally or alternatively be beamformed on a transducing element. In some embodiments, however, Blocks S110 and/or S120 of the method 100 can, however, additionally and/or alternatively include retrieving acoustic signals from a storage device such as a hard drive or an online server. Furthermore, in relation to detecting acoustic signals, the method 100 can additionally or alternatively include processing the set of acoustic signals according to at least one conditioning algorithm. For instance, for a given transmitter/detector pair of transducers, processing the set of acoustic signals can include one or more of: reading and correcting the raw data (detected acoustic signals) for DC variation; implementing a trapezoidal filter to bandpass useful frequencies and cut noise; and implementing any other suitable filter (high pass, low pass, etc.) to filter desired frequencies. Further signal processing can additionally or alternatively include discarding unusable signal such as "muting" in which recorded signal before the transmission wavefront and/or and after the longest applicable receiving time (e.g., "top muting" or "bottom muting"), further noise reduction processes, and other suitable signal processing steps. However, any other suitable conditioning process can additionally or alternatively be used.

Block S130 recites generating, from the set of acoustic signals, a reflection rendering of the volume of tissue, which functions to characterize a distribution of an acoustic reflection parameter within the volume of tissue. Block S130 is preferably implemented at a processing system (e.g., a computer processor, computing system) included with or coupled to the ultrasound tomographic scanner 200 of Blocks S110 and S120, but can additionally or alternatively be implemented at any other suitable processing system. Block S130 preferably includes generation of the reflection rendering from the set of acoustic signals detected in variations of Block S120, but can additionally or alternatively include generation of the reflection rendering using any other suitable data. As such, in one variation, the reflection rendering can utilize raw source data (e.g., raw ultrasound data, "radiofrequency" or RF data), which can be converted into an amplitude-based B-mode ultrasound image, flash B-mode ultrasound image, and/or any other suitable image. The distribution of the acoustic reflection parameter represented in the reflection rendering can characterize a relationship (e.g., ratio, difference, etc.) between the reflected intensity of an acoustic waveform and the incident intensity of an acoustic waveform, but can additionally or alternatively characterize any other suitable acoustic reflection parameter.

Generation of the reflection rendering in Block S130 preferably comprises generation of a set of reflection image slices characterizing the volume of tissue, wherein each reflection image slice (e.g., corresponding to a cross section of tissue) is derived from a distribution of the acoustic reflection parameter as captured within a particular discrete scanning step during scanning of the volume of tissue. Preferably, generation of the reflection rendering includes generating a set of 2D slices representing acoustic reflection, wherein each slice in the set of 2D slices represents a distribution of the acoustic reflection parameter across the slice of tissue, to form a stack of 2D slices for acoustic reflection within the tissue. In a specific example, the stack of 2D slices corresponds to regions of the volume of tissue generated in a posterior-anterior direction (e.g., from a chest wall to a nipple region of a volume of breast tissue); however, in other variations of the specific example, the stack of 2D slices can alternatively correspond to slices of the volume of tissue generated in any other direction (e.g., medial-lateral direction, inferior-superior direction, anterior-posterior direction, direction angled from an anterior-posterior direction, direction angled from a medial-lateral direction, direction angled from an inferior-superior direction, etc.). Each acoustic reflection slice preferably includes multiple elements (e.g., pixels in a grid) such that each element has an associated value of the acoustic reflection parameter for a respective region of the scan region, including the volume of tissue and the acoustic coupling medium (such as the fluid of the tank in which the tissue is submerged). Furthermore, each acoustic reflection slice is preferably a planar slice; however, the stack of slices for sound speed can be generated in any other suitable manner.

Figure 3:
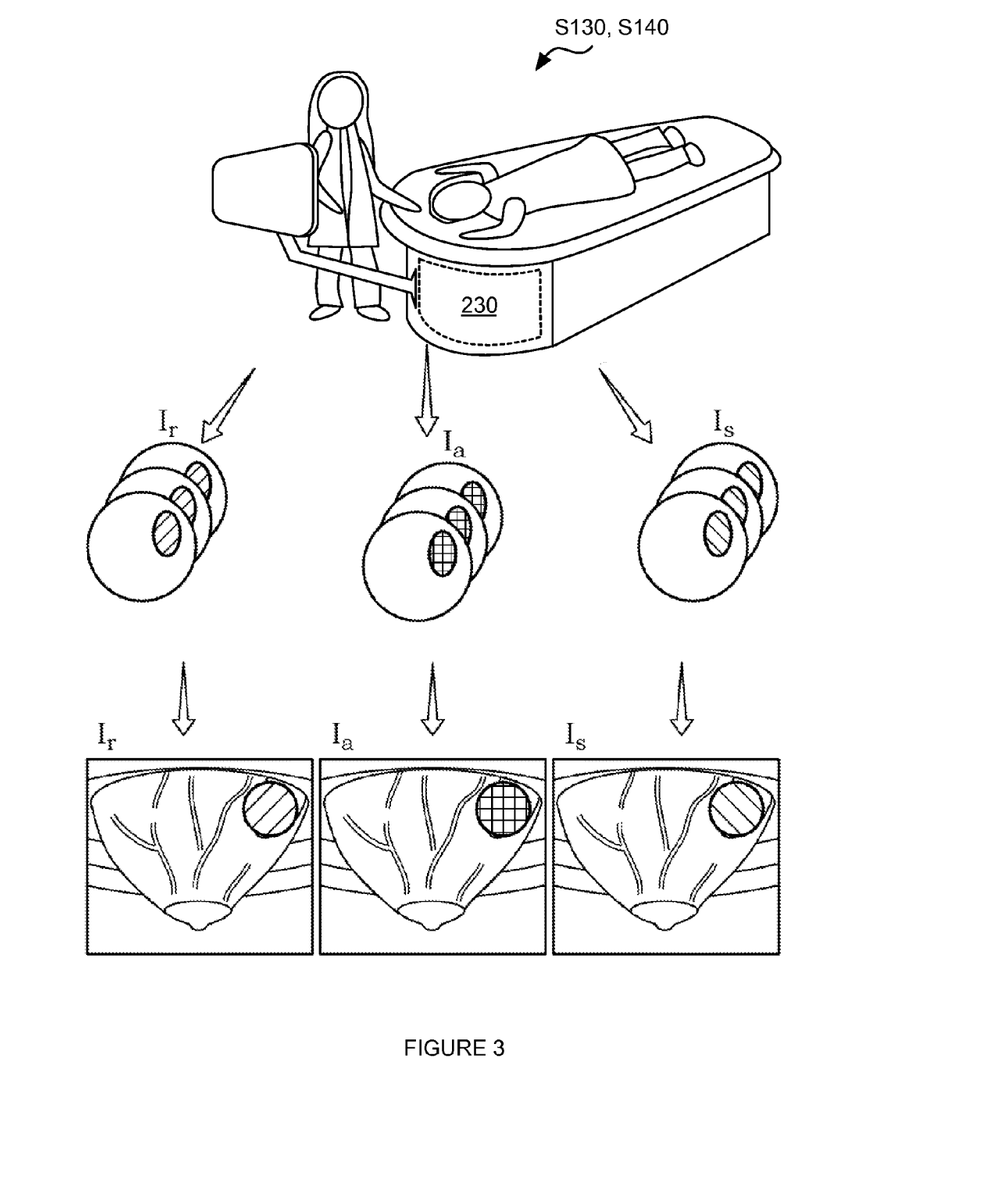
FIG. 3 depicts a portion of an embodiment of a method of generating an enhanced image of a volume of tissue.

As such, the reflection rendering can comprise a stack of 2D renderings that collectively represent the acoustic reflection parameter distribution throughout the volume of tissue (i.e., a 3D volume of tissue). In one variation, the stack of 2D renderings of the reflection rendering ($I_r$), resulting from changes in acoustic impedance of the tissue, provides echo-texture data and anatomical detail for the tissue. However, Block S130 can additionally or alternatively comprise generating a 2D reflection rendering and/or a 3D reflection rendering of the volume of tissue in any other suitable manner. For instance, in a first variation, as shown in FIG. 3, generating a 3D reflection rendering can include generating a set of 2D acoustic reflection slices, wherein each slice in the set of 2D slices represents a distribution of the acoustic reflection parameter (e.g., derived from incident intensity of acoustic waveform and reflected intensity of acoustic waveform) across the slice of tissue, to form a stack of 2D slices for acoustic reflection within the tissue. The stack of 2D acoustic reflection slices can then be transformed into a three-dimensional (3D) acoustic reflection rendering. In a second variation, generating a 3D acoustic reflection rendering can include converting 3D volumetric acoustic data, obtained by scanning the tissue in a 3D manner, directly into a 3D acoustic reflection rendering. Additionally or alternatively, the reflection rendering can be generated using methods as described in U.S. Pat. No. 8,663,113 and/or U.S. Pub. No. 2012/0283566, filed on 23 Jul. 2012, which are each incorporated herein in its entirety by this reference.

Figure 4A:
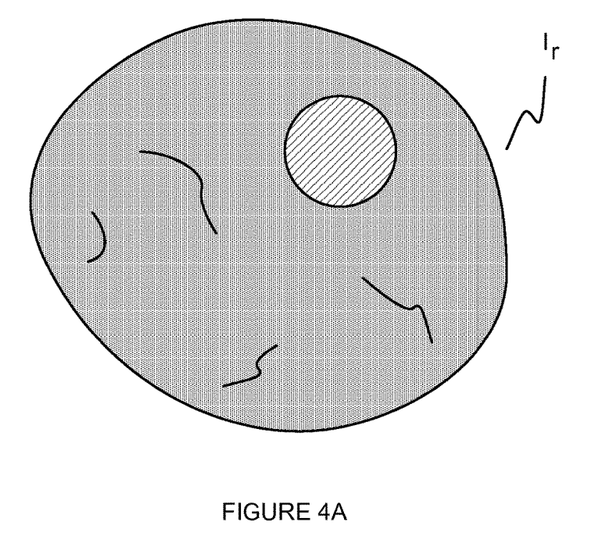
FIGS. 4A-4B depict exemplary outputs of a portion of an embodiment of a method of generating an enhanced image of a volume of tissue.

In some embodiments of Block S130, the reflection rendering of the volume of tissue can characterize a distribution of different tissue types within the volume of tissue, as represented by the distribution of the acoustic reflection parameter across the volume of tissue. As such, the reflection rendering (e.g., a 3D reflection rendering, a 2D reflection rendering, etc.) can characterize a distribution of one or more of: fat tissue (e.g., fatty parenchyma, parenchymal fat, subcutaneous fat, etc.), parenchymal tissue, cancerous tissue, abnormal tissue (e.g., fibrocystic tissue, fibroadenomas, etc.), and any other suitable tissue type within the volume of tissue. In one variation, as shown in FIG. 4A, the reflection rendering represents target masses/regions (e.g., of a cancerous tissue within the volume of tissue) as dark regions (e.g., regions having a medium-to-low intensity of the acoustic reflection parameter), and at least a portion of non-target masses/regions (e.g., of fat tissue) as black regions (e.g., regions having a substantially low intensity of the acoustic reflection parameter). Such a representation can thus be adjusted using a transfer map (e.g., as generated in Block S150), to produce an enhanced reflection image (e.g., as in Block S160). However, in other variations, the reflection rendering can represent target masses/regions or non-target masses/regions in any other suitable manner, to be corrected, enhanced, or adjusted in other variations of Block S160, using any other suitable transfer map.

Block S140 recites: generating, from the set of acoustic signals, at least one of a sound speed map and an attenuation map of the volume of tissue. Block S140 functions to generate at least one additional map that can be used to generate a transfer map that enhances a reflection rendering characterizing the volume of tissue, and can include generation of map(s) from the set of acoustic signals detected in variations of Block S120. Block S140 is preferably implemented using an embodiment, variation, or example of the processing system (e.g., computing system, computer processor) included with or coupled to the ultrasound tomographic scanner 200 described in relation to Block S130 above; however, Block S140 can additionally or alternatively be implemented using any other suitable special purpose processing system.

Similar to Block S130, in variations of Block S140 comprising generation of a sound speed map ($I_s$), the sound speed map is preferably based upon processing of through-transmission signals of the set of acoustic signals, which are received in Blocks S110 and S120 in addition to backscattered signals from the volume of tissue. Preferably, generation of the sound speed map ($I_s$), includes generating a set of 2D slices representing sound speed, wherein each slices in the set of 2D slices represents a distribution of a sound speed parameter (e.g., a speed of sound at each of a set of regions within the volume of tissue) within the tissue, to form a stack of 2D slices for sound speed within the tissue. Preferably, the stack of 2D slices for sound speed generated in variations of Block S140 correspond to (e.g., are associated with the same imaging planes of) the stack of 2D slices for acoustic reflection described in variations of Block S130, such that a transfer map generated from the sound speed map in Block S150 can be directly associated with imaging planes of the reflection rendering of Block S130, thereby facilitating generation of the enhanced reflection rendering. However, in some variations, Block S140 can comprise interpolating sound speed values for planes intermediate to those associated with the set of 2D slices of the sound speed map, in order to determine sound speed values directly associated with the slices of the reflection rendering of Block S130. However, generating sound speed values, from the sound speed map, that can produce a transfer map that is directly associated with the elements of the reflection rendering can be performed in any other suitable manner.

In a specific example, the stack of 2D slices corresponds to regions of the volume of tissue generated in a posterior-anterior direction (e.g., from a chest wall to a nipple region of a volume of breast tissue); however, in other variations of the specific example, the stack of 2D slices can alternatively correspond to slices of the volume of tissue generated in any other direction (e.g., medial-lateral direction, inferior-superior direction, anterior-posterior direction, direction angled from an anterior-posterior direction, direction angled from a medial-lateral direction, direction angled from an inferior-superior direction, etc.). Each sound speed slice preferably includes multiple elements (e.g., pixels in a grid) such that each element has an associated value of the sound speed parameter for a respective region of the scan region, including the volume of tissue and the acoustic coupling medium (such as the fluid of the tank in which the tissue is submerged). Furthermore, each sound speed slice is preferably a planar slice; however, the stack of slices for sound speed can be generated in any other suitable manner.

Generating a sound speed map in Block S130 can additionally or alternatively include generating a 3D sound speed map that is a volumetric representation of the sound speed parameter within the volume of tissue, in a variations similar to those for generation of a 3D reflection rendering. In a first variation, as shown in FIG. 3, generating a 3D sound speed map can include combining a stack of 2D sound speed slices into a three-dimensional (3D) sound speed map. In a second variation, generating a 3D sound speed map can include transforming 3D volumetric acoustic data, obtained by scanning the tissue in a 3D manner, directly into a 3D sound speed map. Additionally or alternatively, the sound speed map can be generated using methods as described in U.S. Pat. No. 8,663,113 and/or U.S. Pub. No. 2012/0283566, filed on 23 Jul. 2012, which are each incorporated herein in its entirety by this reference.

Similar to Block S130, in variations of Block S140 comprising generation of an acoustic attenuation map ($I_a$), generation of an acoustic attenuation map ($I_a$) can include generating a set of 2D slices representing acoustic attenuation, wherein each slice in the set of 2D slices represents a distribution of an acoustic attenuation parameter (e.g., a measure of energy loss of acoustic signal propagation for each of a set of regions within the volume of tissue) within the tissue, to form a stack of 2D slices for acoustic attenuation within the tissue. In a specific example, the stack of 2D slices corresponds to slices of the volume of tissue generated in a posterior-anterior direction (e.g., from a chest wall to a nipple region of a volume of breast tissue); however, in other variations of the specific example, the stack of 2D slices can alternatively correspond to slices of the volume of tissue generated in any other direction (e.g., medial-lateral direction, inferior-superior direction, anterior-posterior direction, direction angled from an anterior-posterior direction, direction angled from a medial-lateral direction, direction angled from an inferior-superior direction, etc.). Preferably, the stack of 2D slices for acoustic attenuation generated in variations of Block S140 correspond to (e.g., are associated with the same imaging planes of) the stack of 2D slices for acoustic reflection described in variations of Block S130, such that a transfer map generated from the attenuation map in Block S150 can be directly associated with imaging planes of the reflection rendering of Block S130, thereby facilitating generation of the enhanced reflection rendering. However, in some variations, Block S140 can comprise interpolating attenuation values for planes intermediate to those associated with the set of 2D slices of the attenuation map, in order to determine attenuation values directly associated with the slices of the reflection rendering of Block S130. However, generating attenuation values, from the attenuation map, that can produce a transfer map that is directly associated with the elements of the reflection rendering can be performed in any other suitable manner.

Each acoustic attenuation slice preferably includes multiple elements (e.g., pixels in a grid) such that each element represents a corresponding attenuation coefficient for a respective region of the scan region, including the volume of tissue and the acoustic coupling medium (such as the fluid of the tank in which the tissue is submerged). In particular, each acoustic attenuation slice can be created using a measure of attenuation of transmission signals and assuming a broad frequency band signal (or any suitable frequency band signal). Additionally or alternatively, each acoustic attenuation slice can be created on a frequency-dependent and/or transducer-dependent basis to account for frequency and directional dependence of absorption and scatter on the signal. Generating an attenuation map can additionally or alternatively include generating a 3D attenuation map that is a volumetric representation of the acoustic attenuation parameter within the volume of tissue, wherein generation of the 3D attenuation map can be implemented in a manner similar to the methods described above with regard to generating a 3D sound speed map and/or a 3D reflection rendering. Additionally or alternatively, the acoustic attenuation map can be generated using methods as described in U.S. Pat. No. 8,663,113 and/or U.S. Pub. No. 2012/0283566, filed on 23 Jul. 2012, which are each incorporated herein in its entirety by this reference.

Figure 4B:
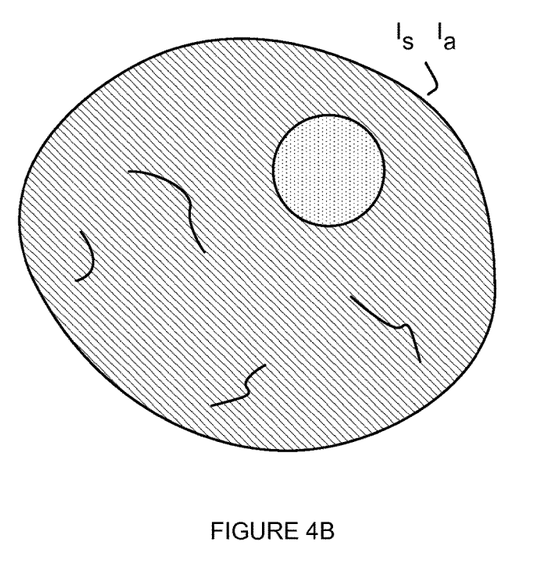

In some embodiments of Block S140, the sound speed map and/or the attenuation map of the volume of tissue can characterize a distribution of different tissue types within the volume of tissue, as represented by the distribution of the acoustic speed parameter/acoustic attenuation parameter across the volume of tissue. As such, the sound speed map (e.g., a 3D acoustic speed rendering, a 2D acoustic speed rendering, etc.) and/or the attenuation map (e.g., a 3D acoustic attenuation rendering, a 2D acoustic attenuation rendering, etc.) can characterize a distribution of one or more of: fat tissue (e.g., fatty parenchyma, parenchymal fat, subcutaneous fat, etc.), parenchymal tissue, cancerous tissue, abnormal tissue (e.g., fibrocystic tissue, fibroadenomas, etc.), and any other suitable tissue type within the volume of tissue. In one variation, as shown in FIG. 4B, the sound speed map represents target masses/regions (e.g., of a cancerous tissue within the volume of tissue) as bright regions (e.g., regions having a high intensity of the acoustic speed parameter), and at least a portion of non-target masses/regions (e.g., of fat tissue) as dark regions (e.g., regions having a substantially low intensity of the acoustic speed parameter). Similarly, in one variation, as shown in FIG. 4B, the acoustic attenuation rendering represents target masses/regions (e.g., of a cancerous tissue within the volume of tissue) as bright regions (e.g., regions having a high intensity of the acoustic speed parameter), and at least a portion of non-target masses/regions (e.g., of fat tissue) as dark regions (e.g., regions having a substantially low intensity of the acoustic attenuation parameter). As such, the representation(s) of acoustic speed and/or acoustic attenuation within the volume of tissue can be used to generate a transfer map (e.g., as in Block S150), to produce an enhanced image (e.g., as in Block S160) of the volume of tissue. However, in other variations, the acoustic speed rendering and/or the acoustic attenuation rendering can represent target masses/regions or non-target masses/regions in any other suitable manner, which can be used to generate a transfer map that can facilitate correction, enhancement, or adjustment of a reflection rendering and/or any other suitable rendering.

Block S150 recites: generating a transfer map based upon a manipulation of at least one of the sound speed map and the attenuation map, which functions to enable generation of the enhanced image of the volume of tissue in variations of Block S160. The transfer map is preferably generated based upon a sound speed map of Block S140, but can additionally or alternatively be generated based upon an attenuation map of Block S140. As such, some variations of the transfer map can be generated based upon a sound speed rendering, an attenuation rendering, or a combination of an acoustic speed rendering and an acoustic attenuation rendering. Furthermore, the transfer map can additionally or alternatively be generated based upon any other suitable parameter generated from the acoustic signals detected in Block S120 and/or any other suitable parameter.

In variations, Block S150 can comprise renormalizing a map S151 to ensure that pixel values of the map(s) do not have undesired values. Block S151 functions to facilitate operations performed (e.g., mathematical operations performed on arrays) using the transfer map and the reflection rendering in Block S160. As such, renormalizing in Block S151 can comprise any one or more of increasing pixel intensity values of a map (e.g., uniformly increasing all intensity ranges by a factor, non-uniformly increasing ranges of intensities by different factor), decreasing pixel intensity values of a map (e.g., uniformly decreasing all intensity ranges by a factor, non-uniformly decreasing ranges of intensities by different factor), scaling pixel intensity values of a map (e.g., uniformly scaling by a factor, non-uniformly scaling ranges of intensities by different factors), performing an absolute value operation on pixel intensities of a map, and performing any other suitable manipulation on the map. In variations wherein the rendering(s) used to generate the transfer map comprise a stack of 2D renderings, the manipulation is preferably performed uniformly across each rendering in the stack of renderings, as well as uniformly across the stack of renderings. However, the manipulation(s) can additionally or alternatively be performed in any suitable manner. In one variation, renormalizing in Block S151 can be based upon values of the reflection rendering (or any other rendering upon which the transfer map is intended to operate), such that the reflection rendering governs the manipulation performed in Block S151. In specific examples, renormalizing can ensure that pixel intensity values of a map (e.g., a sound speed map, an attenuation map, a combined map generated from a sound speed map and an attenuation map, etc.) do not have undesired values (e.g., zero values, negative values, values outside of a range in relation to pixel intensity values of the reflection rendering).

In variations, Block S150 can additionally or alternatively comprise combining maps characterizing different acoustomechanical parameters S152, such that the transfer map is based upon a combination of multiple maps (e.g., a sound speed map, an attenuation map, etc.) characterizing different acoustomechanical parameters. Combining maps can comprise any one or more of: adding pixel intensity values of corresponding regions (e.g., pixel grid regions) of different maps, subtracting pixel intensity values of corresponding regions (e.g., pixel grid regions) of different maps, averaging pixel intensity values of corresponding regions (e.g., pixel grid regions), weighting pixel intensity values of corresponding regions (e.g., pixel grid regions) of different maps (e.g., based upon a correlation between pixel intensity values across renderings characterizing different acoustomechanical parameters), and performing any other suitable combining operation on different maps.

Figure 5:
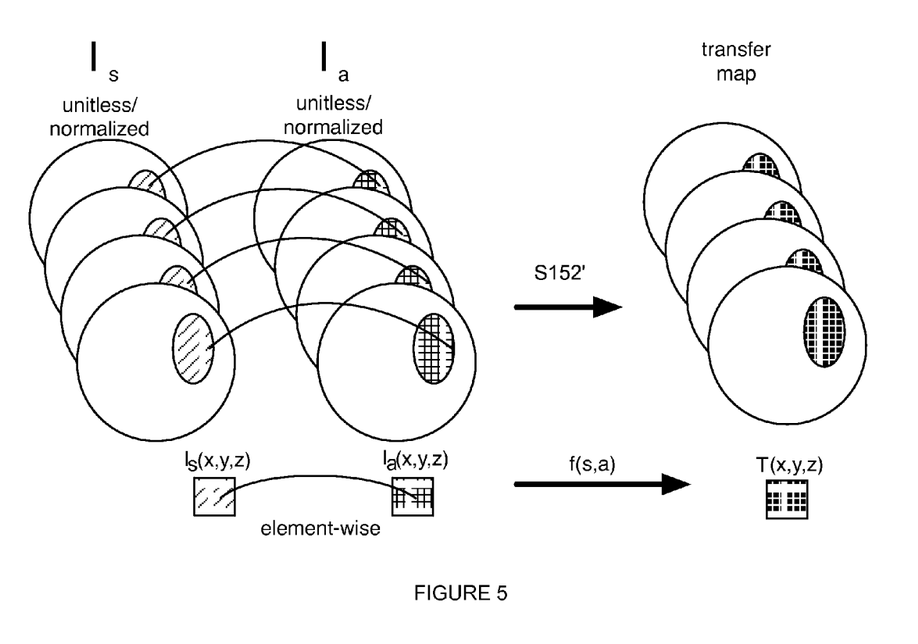
FIG. 5 depicts a variation of a portion of an embodiment of a method of generating an enhanced image of a volume of tissue.

In the variation shown in FIG. 5, Block S152' can comprise combining a map derived from a sound speed map with a map derived from an attenuation map (e.g., for corresponding 2D image slices of a volume of tissue), such that the transfer map is derived from a sound speed representation and an attenuation representation. The map derived from a sound speed map can be a map renormalized according to the variations of renormalization described above, and similarly, the map derived from an attenuation map can be a map renormalized according to the variations of renormalization above. Furthermore, in Block S152', each map that represents a different acoustomechanical parameter can be normalized according to the same scale (e.g., unit-less scale). However, in other variations, each map that represents a different acoustomechanical parameter can be normalized according to different scales (e.g., different unit-less scales), such that at least one of the maps is weighted differently than the other map(s) in performing the combination of Block S152.

In more detail, combining a set of sound speed parameter values of the sound speed map and a corresponding set of acoustic attenuation parameter values of the acoustic attenuation map can comprise pairing each slice in the stack of 2D slices of sound speed with a corresponding slice in the stack of 2D slices of acoustic attenuation, as shown in FIG. 5, and performing an operation f(s,a) across each sound speed slice with its paired acoustic attenuation slice, in an element-wise manner (e.g., across a given slice, across a region of interest) to form a combined acoustomechanical parameter map as a transfer map. As indicated above, the operation f(s,a) can comprise one or more of: an addition operation, an averaging operation, a scaling operation, a weighting operation, a subtraction operation, and any other suitable operation.

In a specific example, Block S152 can include averaging (e.g., performing element-wise averaging between) the normalized and unit-less values of each sound speed slice and its paired acoustic attenuation slice to form the transfer map comprising a stack of 2D slices. As such, the transfer map of this variation of Block S152 includes a set of elements, each representing an average, normalized, and unit-less value of sound speed and acoustic attenuation, such that the combined acoustomechanical parameter map represents a distribution of an average of sound speed and attenuation across a region of the volume of tissue. In variations of the specific example, at least one of the set of sound speed splices and the set of attenuation slices can be weighted prior to combination, in generating the transfer map of Block S150. Combination can, however, be implemented in any other suitable manner.

Block S151 and/or Block S152 can be performed in any suitable order, with any suitable number of repetitions in generating the transfer map. As such, one example of Block S150 can include combining an acoustic speed rendering with an acoustic attenuation rendering (e.g., fusing the two renderings or combining them mathematically into a single image), and then renormalizing the fused rendering to produce the transfer map. Another example of Block S150 can include renormalizing each of an acoustic speed rendering and an acoustic attenuation rendering, and then fusing the two renderings to produce the transfer map. In yet another example, the transfer map can be based upon a renormalization of one of an acoustic speed rendering and an acoustic attenuation rendering. However, the transfer map of Block S150 can be generated in any other suitable manner.

Block S160 recites: rendering an enhanced image of the volume of tissue, based upon processing of the reflection rendering with the transfer map, which functions to produce an enhanced image that facilitates detection and/or analysis of target objects within the volume of tissue. Block S160 preferably comprises a modification of a reflection rendering generated in Block S130 using the transfer map (e.g., a combining the reflection image and the transfer map using a mathematical operation), but can additionally or alternatively comprise performing an operation on any other suitable rendering with the transfer map. The operation can include any one or more of: a division operation, a multiplication operation, an exponential operation, a logarithmic operation, and any other suitable operation. In one variation, the operation can be performed for each pixel $p_{x,y,z}$ of a rendering (e.g., a reflection rendering), where x and y represent coordinate locations within a two dimensional plane (e.g., an x-y plane), and z represents a location along another axis (e.g., a location of an image slice of a stack of 2D image slices). As such, for each pixel $p_{x,y,z}$ location of a rendering, a transfer map value corresponding to the $p_{x,y,z}$ location can be used to transform the pixel intensity value at the $p_{x,y,z}$ location. However, any other suitable coordinate definition can be used.

Figure 6:
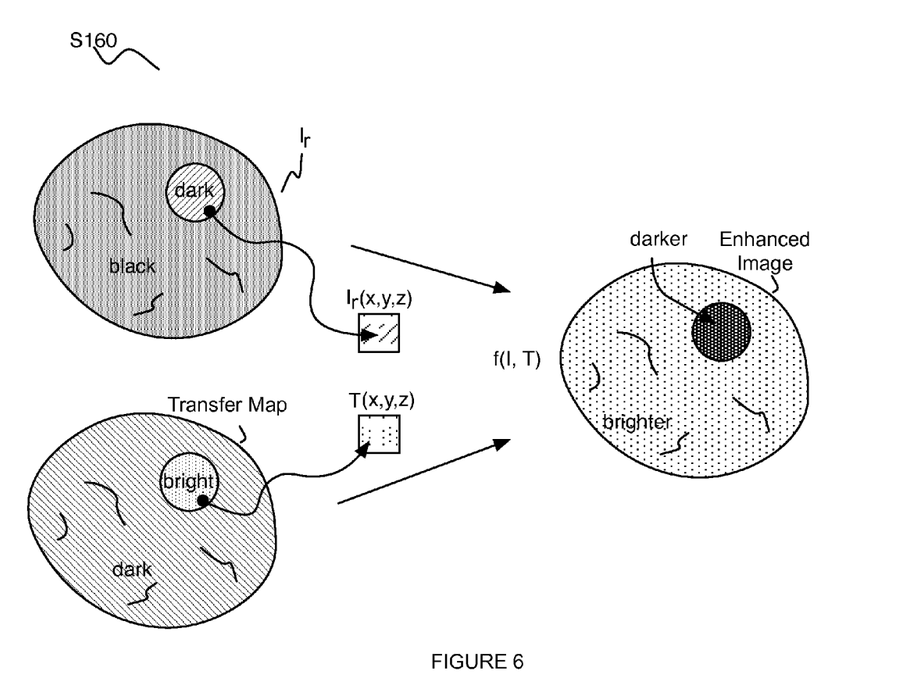
FIG. 6 depicts an example of generating an enhanced image of a volume of tissue.

In one example, as shown in FIG. 6, wherein the reflection rendering $I_r$ represents target regions (e.g., of a cancerous tissue within the volume of tissue) as dark regions (e.g., regions having a medium-to-low intensity of the acoustic reflection parameter) and non-target regions (e.g., of fat tissue) as black regions (e.g., regions having a substantially low intensity of the acoustic reflection parameter), Block S160 can comprise dividing an intensity of each pixel $p_{x,y,z}$ of a reflection rendering $I_r$ of the volume of tissue by a value of the transfer map T corresponding to the location of the $p_{x,y,z}$ pixel. As such, the transfer map can represent the target regions (e.g., of a cancerous tissue within the volume of tissue) as bright regions (e.g., regions having a high intensity value), and at least a portion of non-target masses/regions (e.g., of fat tissue) as dark regions (e.g., regions having a substantially low intensity value), such that dividing reflection rendering values by corresponding transfer map values decreases pixel intensity values corresponding to target regions, thus making them "darker", and increases pixel intensity values corresponding to non-target regions, thus making them "brighter", as shown in FIG. 6.

In more detail, for a reflection value $Ir(x_1, y_1, z_1)$ of a target mass that has a high intensity value, dividing the reflection value by a corresponding low value of the transfer map $T(x_1, y_1, z_1)$ results in an enhanced image value $E(x_1, y_1, z_1)$ that has an even higher intensity value (i.e., darker). For a reflection value $Ir(x_2, y_2, z_2)$ of a non-target mass that has a very high intensity value, dividing the reflection value by a corresponding high intensity value of the transfer map $T(x_2, y_2, z_2)$ results in an enhanced image value $E(x_2, y_2, z_2)$ that has a lower intensity value (i.e., brighter), as shown in FIG. 6. Variations of the specific example can, however, include performing any other suitable operation(s) using any suitable rendering and/or transfer function. For instance, the values of the transfer map can be scaled to value ranges that enhance the enhanced image to any degree. For instance, scaling values of the transfer map to value ranges between 0 and 1 can produce an enhanced image that is enhanced to a greater degree, while scaling values of the transfer map to value ranges between much greater than 1 can produce an enhanced image that is enhanced to a lesser degree.

Similar to Block S151, variations of the method 100 can additionally include renormalization of the enhanced image after generating the enhanced image to bring intensity values of the enhanced image within a desired range. As such, renormalizing after Block S160 can comprise any one or more of increasing pixel intensity values of the enhanced image (e.g., uniformly increasing all intensity ranges by a factor, non-uniformly increasing ranges of intensities by different factor), decreasing pixel intensity values of the enhanced image (e.g., uniformly decreasing all intensity ranges by a factor, non-uniformly decreasing ranges of intensities by different factor), scaling pixel intensity values of the enhanced image (e.g., uniformly scaling by a factor, non-uniformly scaling ranges of intensities by different factors), performing an absolute value operation on pixel intensities of the enhanced image, and performing any other suitable manipulation on the enhanced image. In variations wherein the enhanced image comprises a stack of 2D renderings, the manipulation is preferably performed uniformly across each rendering in the stack of renderings, as well as uniformly across the stack of renderings. However, the renormalization manipulation(s) for the enhanced image can additionally or alternatively be performed in any suitable manner.

The method 100 can, however, include any other suitable blocks or steps that facilitate detection, processing, and/or analyzing of acoustic signals generated from a volume of tissue of the user in a manner that provides an enhanced representation of the volume of tissue.

2. System

As shown in FIGS. 2A-2C, an embodiment of a system 200 for generating an enhanced imaged of a volume of tissue, comprises: a transducer 220 configured to receive the volume of tissue and comprising an array of ultrasound transmitters 110 and an array of ultrasound receivers 120, the array of ultrasound transmitters no configured to emit acoustic waveforms toward the volume of tissue and the array of ultrasound receivers 120 configured to detect a set of acoustic signals derived from acoustic waveforms transmitted through the volume of tissue; a computer processor 210 in communication with the transducer 220, the computer processor 210 comprising: a first module 212 configured to output a reflection rendering of a region of the volume of tissue, the region including a set of elements; a second module 214 configured to output a sound speed map of the region of the volume of tissue; a third module 216 configured to receive outputs of the second module and to generate a transfer map derived from renormalization of the sound speed map; a fourth module 218 configured to generate an enhanced image of the volume of tissue, upon performing element-wise division between elements of the reflection rendering and elements of the transfer map; and a display 290 in communication with the computer processor 210 and configured to render the enhanced image of the volume of tissue.

The system 200 is preferably configured to perform an embodiment, variation, or example of the method 100 described above; however, the system 200 can additionally or alternatively be configured to perform any other suitable method.

The FIGURES illustrate the architecture, functionality and operation of possible implementations of systems, methods and computer program products according to preferred embodiments, example configurations, and variations thereof. In this regard, each block in the flowchart or block diagrams may represent a module, segment, step, or portion of code, which comprises one or more executable instructions for implementing the specified logical function(s). It should also be noted that, in some alternative implementations, the functions noted in the block can occur out of the order noted in the FIGURES. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The method 100 and/or system 200 of the preferred embodiment can be embodied and/or implemented at least in part as machine configured to receive a computer-readable medium storing computer-readable instructions. The instructions are preferably executed by computer-executable components preferably integrated with the system and one or more portions of the processor and/or analysis engine. The computer-readable medium can be implemented in the cloud, and/or stored on any suitable computer-readable media such as RAMs, ROMs, flash memory, EEPROMs, optical devices (CD or DVD), hard drives, solid state drives, or any suitable device. The computer-executable component is preferably a general or application specific processor, but any suitable dedicated hardware or hardware/firmware combination device can alternatively or additionally execute the instructions.

As a person skilled in the art will recognize from the previous detailed description and from the figures and claims, modifications and changes can be made to the preferred embodiments of the invention without departing from the scope of this invention defined in the following claims.

We claim:

1. A method for generating an enhanced image of a volume of tissue, the method comprising:

with a transducer comprising an array of ultrasound transmitters and an array of ultrasound receivers and configured to surround the volume of tissue, emitting acoustic waveforms toward the volume of tissue with the array of ultrasound transmitters;

detecting, with the array of ultrasound receivers, a set of acoustic signals derived from acoustic waveforms interacting with the volume of tissue;

at a computing system in communication with the transducer, generating, from the set of acoustic signals, a reflection rendering of a region of the volume of tissue, the region including a set of elements;

at the computing system, generating, from the set of acoustic signals, a sound speed map of the region of the volume of tissue;

at the computing system, generating a transfer map by renormalizing a set of sound speed parameter values of the sound speed map, the set of sound speed parameter values associated with the set of elements of the region of the volume of tissue;

transforming the reflection rendering into an enhanced image performing element-wise division between elements of the reflection rendering and elements of the transfer map, across the set of elements of the region, thereby decreasing intensity values corresponding to a target region; and at a display in communication with the computing system, rendering the enhanced image of the volume of tissue, wherein the target region is darker in the enhanced image than in the reflection rendering.

2. The method of claim 1, wherein generating the reflection rendering of the region of the volume of breast tissue comprises generating a set of reflection slices associated with coronal slices through a volume of breast tissue, and wherein generating the sound speed map for the region of the volume of breast tissue comprises generating a set of sound speed slices associated with a set of coronal slices through the volume of breast tissue.

3. The method of claim 2, wherein renormalizing the set of sound speed parameter values of the sound speed map comprises conditioning the sound speed map to remove negative values of the sound speed map, prior to performing element-wise division between elements of the reflection rendering and elements of the transfer map.

4. The method of claim 1, wherein generating the transfer map comprises generating, from the set of acoustic signals, an attenuation map of the region of the volume of tissue, and generating a combined map derived from the sound speed map and the attenuation map.

5. The method of claim 4, wherein generating the combined map comprises performing element-wise averaging of values derived from the sound speed map and corresponding values derived from the attenuation map.

6. The method of claim 1, wherein renormalizing comprises at least one of: increasing pixel intensity values of the sound speed map, scaling pixel intensity values of the sound speed map, and performing an absolute value operation on pixel intensities of the sound speed map.

7. The method of claim 1, wherein rendering the enhanced image of the volume of tissue comprises providing indication of the target region, associated with a cancerous mass, as darker than a non-target region, associated with fat tissue.

8. A method for generating an enhanced image of a volume of tissue, the method comprising:

with a transducer comprising an array of ultrasound transmitters and an array of ultrasound receivers and configured to surround the volume of tissue, emitting acoustic waveforms toward the volume of tissue with the array of ultrasound transmitters;

detecting, with the array of ultrasound receivers, a set of acoustic signals derived from acoustic waveforms interacting with the volume of tissue;

at a computing system in communication with the transducer, generating, from the set of acoustic signals, a reflection rendering of a region of the volume of tissue, the region including a set of elements;

at the computing system, generating, from the set of acoustic signals, at least one of a sound speed map and an attenuation map of the region of the volume of tissue;

at the computing system, generating a transfer map derived from at least one of:

1) a set of sound speed parameter values of the sound speed map and 2) a set of acoustic attenuation parameter values of the acoustic attenuation map, the set of sound speed parameter values and the set of acoustic attenuation parameters associated with the set of elements of the region of the volume of tissue;

transforming the reflection rendering into an enhanced image by processing the reflection rendering and the transfer map, thereby decreasing intensity values corresponding to a target region; and at a display in communication with the computing system, rendering an enhanced image of the volume of tissue, wherein the target region is darker in the enhanced image than in the reflection rendering.

9. The method of claim 8, wherein generating the reflection rendering of the region of the volume of breast tissue comprises generating a set of reflection slices associated with coronal slices through a volume of breast tissue, and wherein generating the transfer map comprises generating the transfer map from a combination of the sound speed map and the attenuation map.

10. The method of claim 9, wherein generating the combination of the sound speed map and the attenuation map comprises performing element-wise averaging of values derived from the sound speed map and corresponding values derived from the attenuation map.

11. The method of claim 8, wherein generating the transfer map includes renormalizing the set of sound speed parameter values of the sound speed map, and wherein renormalizing comprises conditioning the sound speed map to remove negative values of the sound speed map.

12. The method of claim 11, wherein renormalizing comprises at least two of: increasing pixel intensity values of the sound speed map, scaling pixel intensity values of the sound speed map, and performing an absolute value operation on pixel intensities of the sound speed map.

13. The method of claim 12, wherein processing of the reflection rendering with the transfer map includes performing element-wise division between elements of the reflection rendering and elements of the transfer map, across the set of elements of the region.

14. The method of claim 8, wherein rendering the enhanced image of the volume of tissue comprises providing indication of the target region, associated with a cancerous mass, as darker than a non-target region, associated with fat tissue.

15. A system for generating an enhanced imaged of a volume of tissue, the system comprising:

a transducer configured to receive the volume of tissue and comprising an array of ultrasound transmitters and an array of ultrasound receivers, the array of ultrasound transmitters configured to emit acoustic waveforms toward the volume of tissue and the array of ultrasound receivers configured to detect a set of acoustic signals derived from acoustic waveforms transmitted through the volume of tissue;

a computer processor in communication with the transducer, the computer processor comprising instructions which when executed cause the processor to:

output a reflection rendering of a region of the volume of tissue, the region including a set of elements;

output a sound speed map of the region of the volume of tissue;

receive outputs of the second module and to generate a transfer map derived from by renormalization of the sound speed map; and generate an enhanced image of the volume of tissue, by performing element-wise division between elements of the reflection rendering and elements of the transfer map, thereby decreasing intensity values corresponding to a target region; and a display in communication with the computer processor and configured to render the enhanced image of the volume of tissue, wherein the target region is darker in the enhanced image than in the reflection rendering.

16. The system of claim 15, wherein the transducer comprises a ring transducer, wherein the array of ultrasound transmitters and the array of ultrasound receivers are arranged about the ring transducer in an axially symmetric manner about an opening of the ring transducer, wherein the opening of the ring transducer is configured to receive the volume of tissue.

17. The system of claim 16, wherein the transducer is configured to pass along the volume of tissue, submerged in an imaging tank with a coupling medium, in an anterior-posterior direction in generating coronal slices of the volume of tissue.

18. The system of claim 16, wherein the instructions when executed cause the processor to perform at least one of: increasing pixel intensity values of the sound speed map, scaling pixel intensity values of the sound speed map, and performing an absolute value operation on pixel intensities of the sound speed map in generating the transfer map.

19. The system of claim 16, wherein the instructions when executed cause the processor to generate the enhanced image upon performing element-wise division between elements of the reflection rendering and elements of the transfer map, across the set of elements of the region.

20. The system of claim 19, wherein the display, in cooperation with the computer processor, is configured to provide indication of the target region, associated with a cancerous mass, as darker than a non-target region, associated with fat tissue.

* * * * *

UNITED STATES PATENT AND TRADEMARK OFFICE
CERTIFICATE OF CORRECTION

| | | |
|---|---|---|
| PATENT NO. | : 10,285,667 B2 | Page 1 of 1 |
| APPLICATION NO. | : 14/819091 | |
| DATED | : May 14, 2019 | |
| INVENTOR(S) | : Nebojsa Duric, Peter Littrup and Cuiping Li | |

It is certified that error appears in the above-identified patent and that said Letters Patent is hereby corrected as shown below:

In the Specification

In Column 1, Line 11, insert following header and paragraph:
--STATEMENT AS TO FEDERALLY SPONSORED RESEARCH
This invention was made with Government support under Grant R44CA165320 awarded by the National Institutes of Health (NIH) through the National Cancer Institute. The Government has certain rights in the invention.--

Signed and Sealed this
Thirtieth Day of July, 2024

Katherine Kelly Vidal
*Director of the United States Patent and Trademark Office*